United States Patent [19]

Spivack et al.

[11] Patent Number: 4,642,382
[45] Date of Patent: Feb. 10, 1987

[54] 1H-POLYALKYL-PHOSPHORINANES

[75] Inventors: John D. Spivack; Stephen D. Pastor, both of Spring Valley, N.Y.; Paul Odorisio, Palisades Park, N.J.

[73] Assignee: Ciba-Geigy Corporation, Ardsley, N.Y.

[21] Appl. No.: 756,123

[22] Filed: Jul. 18, 1985

Related U.S. Application Data

[62] Division of Ser. No. 540,238, Oct. 11, 1983, Pat. No. 4,539,421.

[51] Int. Cl.$^4$ .............................. C07F 9/50; C07F 9/53
[52] U.S. Cl. ........................ 568/12; 524/100; 524/104; 560/105; 564/16
[58] Field of Search ............................ 568/12; 564/16

[56]        References Cited
        U.S. PATENT DOCUMENTS

| | | | |
|---|---|---|---|
| 2,160,915 | 6/1939 | Schreiber | 568/12 X |
| 3,079,427 | 2/1963 | Peters | 568/12 X |
| 3,086,053 | 4/1963 | Wagner | 568/12 |
| 3,105,096 | 9/1963 | Welcher | 568/12 |
| 3,225,103 | 12/1965 | Welcher | 568/12 |
| 3,352,919 | 11/1967 | Welcher | 568/12 |

FOREIGN PATENT DOCUMENTS

| | | | |
|---|---|---|---|
| 963417 | 7/1964 | United Kingdom | 568/12 |
| 971669 | 9/1964 | United Kingdom | 568/12 |

*Primary Examiner*—Helen M. S. Sneed
*Attorney, Agent, or Firm*—Harry Falber

[57]          ABSTRACT

The title compounds correspond to the formula

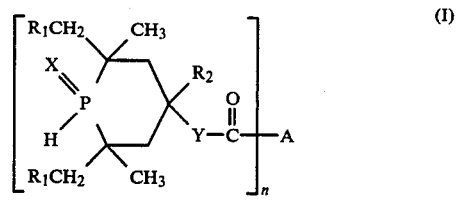

and are useful as stabilizers for organic polymers and lubricating oils to counteract the degradative effects of heat, light and air.

6 Claims, No Drawings

1H-POLYALKYL-PHOSPHORINANES

This is a divisional of application Ser. No. 540,238 filed on Oct. 11, 1983, now U.S. Pat. No. 4,539,421.

Organic polymeric materials such as plastics and resins, and lubricating and mineral oils are subject to thermal, oxidative and photo-degradation. A great variety of stabilizers are known in the art for stabilizing a diversity of substrates. Their effectiveness varies depending upon the causes of degradation and the substrate stabilized. In general, it is difficult to predict which stabilizer will be most effective and most economical for any one area of application. For example stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of discoloration may require inhibiting reactions which yield new chromophores or color bodies in the substrate or stabilizer. Problems of process stability and incompatibility must also be considered.

It has now been determined that the 1H-polyalkyl-phosphorinane esters and amides of this invention possess an unusual combination of desirable properties which make them particularly effective and useful as stabilizers. The compounds are particularly effective in protecting polyolefins, high impact polystyrene, rubbers such as polybutadiene and styrene-butadiene rubber, and other elastomers wherein retention of elasticity and inhibition of cross-linking, crazing, discoloration, odor formation and exudation are basic requirements.

It has also been determined that the carbon-substituted 1H-phosphorinanes such as the polyalkyl-4-hydroxy-1H-phosphorinanes or the polyalkyl-4-amino-1H-phosphorinanes utilized to prepare the above noted esters and amides are novel and thus constitute a further embodiment of this invention.

With regard to the latter starting materials, it is to be noted that carbon-substituted 1-alkyl and 1-aryl phosphorinanones have been disclosed by R. P. Welcher and N. E. Day, J. Org. Chem., 27, 1824 (1962) while carbon-unsubstituted 1H-phosphorinanes have been disclosed by L. D. Quin, The Heterocyclic Chemistry of Phosphorus", J. Wiley 1981 New York, chp. 3.

It is the primary object of this invention to provide a class of 1H-polyalkyl-phosphorinane esters and amides which exhibit a broad range of improved stabilization performance characteristics.

Various other objects and advantages of this invention will become evident from the following description thereof.

The compounds of the invention correspond to the formula I

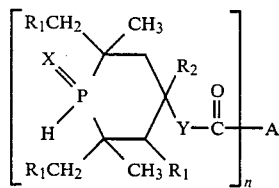

(I)

wherein $R_1$ and $R_2$ independently are hydrogen or $C_1$-$C_8$ alkyl;

X is —O—, —S— or a lone pair of electrons;

Y is —O— or —N($R_3$)— where $R_3$ is hydrogen or $C_1$-$C_{12}$ alkyl;

n is 1 to 5; and

A is an n-valent aliphatic hydrocarbon of 1 to 20 carbon atoms, an n-valent aromatic or aromatic aliphatic hydrocarbon of 6 to 20 carbon atoms or an n-valent radical of 5-7-membered heterocyclic compound.

$R_1$ and $R_2$ as $C_1$-$C_8$ alkyl are straight-chain or branched alkyl such as methyl, ethyl, n-propyl, isopropyl, n-butyl, sec-butyl, tert-butyl, n-pentyl, tert-pentyl, n-hexyl, 2-ethylhexyl, n-octyl and 1,1,3,3,-tetramethylbutyl. $R_3$ as $C_1$-$C_{12}$ alkyl includes the same members as defined hereinabove for $R_1$ and $R_2$ and is additionally e.g. nonyl, decyl annd dodecyl.

A as a monovalent aliphatic hydrocarbon can be e.g. $C_1$-$C_{18}$ alkyl, including the members defined hereinabove for $R_1$, $R_2$ and $R_3$ and in addition, tridecyl, tetradecyl, pentadecyl, hexadecyl, heptadecyl and octadecyl, or $C_5$-$C_6$ cycloalkyl such as cyclopentyl or cyclohexyl.

A as a monovalent aromatic hydrocarbon can be, for example, phenyl which can be substituted by $C_1$-$C_4$ alkyl and hydroxy, such as e.g. tolyl, xylyl, mesityl, 3,5-di-methyl-4-hydroxy-phenyl, 3,5-di-tert-butyl-4-hydroxyphenyl, etc. or $C_7$-$C_{10}$ aralkyl substituted by $C_1$-$C_4$ alkyl and hydroxy such as for example 3,5-di-tert-butyl-4-hydroxybenzyl or particularly 2-(3,5-di-tert-butyl-4-hydroxyphenyl)ethyl.

A as a bivalent hydrocarbon can be e.g. straight-chain or branched $C_2$-$C_{10}$ alkylene such as, for example, ethylene, trimethylene, tetramethylene, pentamethylene, 2,2-dimethylpropane-1,3diyl, hexamethylene, heptamethylene, octamethylene, decamethylene, 2,2-pentamethylenepropane-1,3-diyl and cyclohexylene or $C_6$-$C_{10}$ arylene such as phenylene, phenylene substituted by one or more $C_1$-$C_4$ alkyl or naphthylene.

A as a trivalent, tetravalent or pentavalent hydrocarbon is for example a group of the following formulae

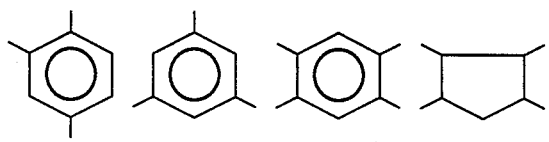

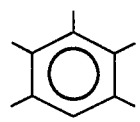

A as a radical of a 5-7-membered heterocyclic compound can be for example a group of the following formulae

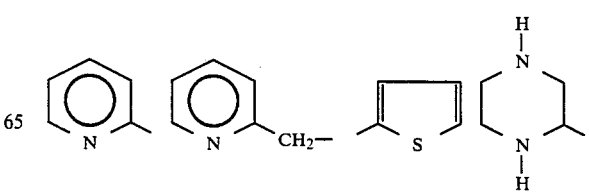

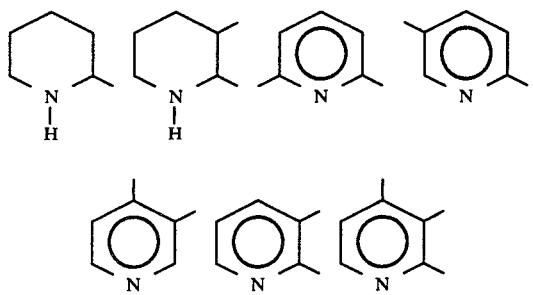

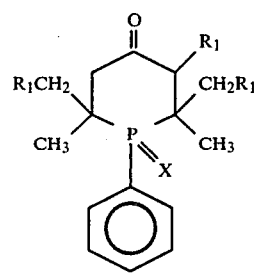

Preferred compounds are those wherein $R_1$ and $R_2$ are hydrogen, X is —O— or a lone pair of electrons, Y is —O—, n is 1 or 2, especially 2, A is $C_1$-$C_8$ alkyl or $C_7$-$C_{10}$ aralkyl substituted by $C_1$-$C_4$ alkyl and hydroxy, particularly 2-(3,5-di-tert-butyl-4-hydroxyphenyl)ethyl when n is 1 and $C_4$-$C_8$ alkylene when n is 2.

The compounds of the present invention are prepared by any of the well known esterification or amidation methods from the reaction of acids of the formula A-$(COOH)_n$ (or their derivatives such as halides, anhydrides or lower alkyl esters particularly methyl ester) with a compound of formula II

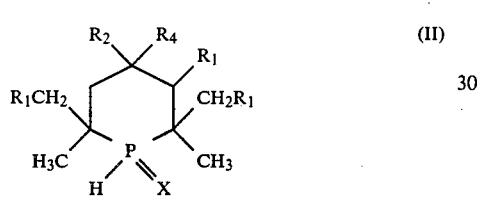

wherein
$R_4$ is hydroxy or a group —$NHR_3$ and n, $R_1$, $R_2$, $R_3$ and X have the meanings given above.

Particularly suitable acids are carboxylic acids with 2 to 18 carbon atoms e.g. acetic acid, propionic acid, butyric acid, 2,2-dimethylpropionic acid, heptanoic acid, lauric acid, myristic acid, palmitic acid, stearic acid, cyclohexane carboxylic acid, benzoic acid, 3-(3,5-di-tert-butyl-4-hydroxyphenyl)propionic acid, succinic acid, adipic acid, azelaic acid, sebacic acid, phthalic acid, 1,1-cyclohexane-diacetic acid, 1,2,4-benzenetricarboxylic acid, 1,3,5-benzenetricarboxylic acid, 1,2,4,5-benzene-tetracarboxylic acid, benzenepentacarboxylic acid, 1,2,3,4-cyclopentane-tetracarboxylic acid, 2-thiophenecarboxylic acid, 2-pyrazinecarboxylic acid, 2-pyridylacetic acid, 2-pyridinecarboxylic acid, 2,3-piperidinedicarboxylic acid, 2,6-pyridinedicarboxylic acid, 2,5-pyridinedicarboxylic acid, 3,4-pyridinedicarboxylic acid and 2,3,4-pyridinetricarboxylic acid.

As previously noted, the compounds of formula II are novel and constitute a further embodiment of the present invention. The compounds of formula II, wherein $R_4$ is hydroxy can be prepared as follows:

Initially, phenylphosphine is reacted with divinyl ketones of the formula III

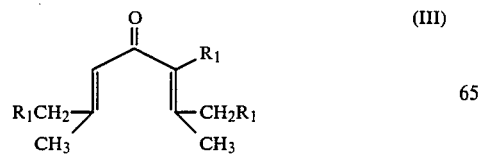

to yield phosphorinanones of the formula IV

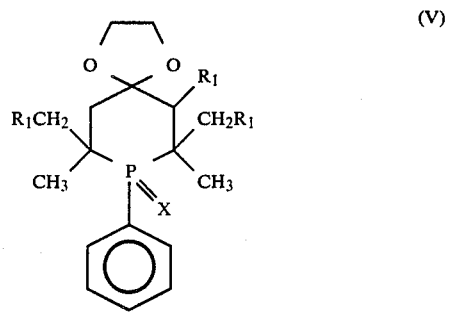

This procedure is exemplified by R. P. Welcher and N. E. Day, J. Org. Chem, 27, 1824 (1962). The preferred divinyl ketones include phorone and 3,4,7-trimethyl-nona-3,6-diene-5-one.

The carbonyl group of formula IV is then protected to yield the 1,3-dioxolane of formula V.

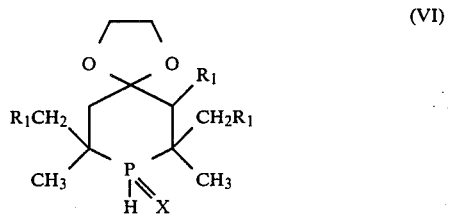

by means of the reaction of IV with ethylene glycol using an acid catalyst according to known methods (e.g. J. March, Advanced Organic Chemistry, p. 810, McGraw-Hill, New York, 1977).

The 1H-phosphorinane of formula VI

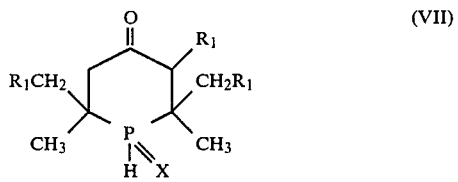

is then obtained by reduction to remove the phenyl substituent of V. The most appropriate method has been found to be the reduction of V with lithium metal in a suitable solvent of which tetrahydrofuran is particularly preferred.

The removal of the 1,3-dioxolane protecting group then leads to the 1H-phosphorinanone of the formula VII.

Many methods are known for the removal of 1,3-dioxolane protecting groups of which the treatement with aqueous mineral acid, e.g. hydrochloric acid, is particularly suitable.

Reduction of the ketone moiety of VII by any of the common methods, e.g. the treatment with lithium tetrahydroaluminate, sodium borohydride, diisobutylaluminum hydride, catalytic hydrogenation, dissolving metal reduction, etc., can be used to obtain the alcohol of formula II, wherein $R_2$ is hydrogen. Alternately, the addition of metal alkyls (e.g. methyl grignard, methyl lithium, butyl lithium, etc.) according to known methods can be used to prepare the tertiary alcohols of formula II, wherein $R_2$ is $C_1$–$C_8$ alkyl.

The compounds of the formula II, wherein $R_4$ is —$NHR_3$ can be prepared from the ketone of the formula VII by conventional reductive amination reactions, e.g. reductive amination of VII with an amine of the formula $H_2NR_3$ and sodium borohydride.

Methods are also known for converting P(III) compounds (compounds of formula I or II, wherein X is a lone pair of electrons) to P(V) compounds (compounds of formula I or II, wherein X is oxygen) including oxidation with meta-chloroperoxybenzoic acid, oxygen or hydrogen peroxide. One particularly satisfactory oxidizing agent is aqueous hydrogen peroxide. The P(III) compound is dissolved in an appropriate solvent e.g. toluene, and mixed with an aqueous solution of hydrogen peroxide until the required oxidation is complete.

The compounds of the formulae I and II wherein X is sulfur can be prepared by known methods e.g. by the reaction of the corresponding phosphine (compounds of formulae I or II wherein X is a lone pair of electrons) with sulfur.

The 1H-phosphorinane esters and amides of this invention are particularly effective in stabilizing organic materials such as plastics, polymers and resins in addition to mineral and synthetic fluids such as lubricating oils, circulating oils, etc.

Substrates in which the compounds of this invention are particularly useful are polyolefins such as polyethylene and polypropylene, polystyrene, including impact polystyrene, butadiene rubber, ABS resin, SBR, isoprene as well as natural rubber.

In general polymers which can be stabilized include:
1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.
2. Mixtures of the polymers mentioned under (1), for example mixtures of polypropylene with polyisobutylene.
3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.
4. Polystyrene, poly-(p-methylstyrene).
5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.
6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA- or AES-polymers.
7. Halogen-containing polymers, such as polychloroprene, chlorinated rubbers, chlorinated or sulfochlorinated polyethylene, epichlorohydrine homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.
8. Polymers which are derived from $\alpha,\beta$-unsaturated acids and derivatives thereof, such as polyacrylates and polymethacrylates, polyacrylamide and polyacrylonitrile.
9. Copolymers from the monomers mentioned under (8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.
10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.
11. Homopolymers and copolymers of cyclic esters, such as polyalkylene glycols, polyethylene oxide, polypropylene oxide or copolymers thereof with bis-glycidyl ethers.
12. Polyacetals, such as polyoxymethylene and those polyoxymethylenes which contain ethylene oxide as comonomer.
13. Polyphenylene oxides and sulfides, and mixtures of polyphenylene oxides with polystyrene.
14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).
15. Polyamides and copolyamides which are derived from diamines and dicarboxylic acids and/or from aminocarboxylic acids or the corresponding lactams, such as polyamides 4, polyamide 6, polyamide 6/6, polyamide 6/10, polyamides 11, polyamide 12, poly- 2,4,4-trimethylhexamethylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.
17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2,-(4-hydroxyphenyl)-propane]terephthalate and polyhydroxybenzoates as well as block-copolyether-esters derived from polyethers having hydroxyl end groups.
18. Polycarbonates.
19. Polysulfones, polyethersulfones and polyetherketones.
20. Crosslinked polymers which are derived from aldehydes on the one hand and phenols, ureas and melamines on the other hand, such as phenol/formaldehyde resins, urea/formaldehyde resins and melamine/formaldehyde resins.
21. Drying and non-drying alkyd resins.
22. Unsaturated polyester resins which are derived from copolyesters of saturated and unsaturated dicarboxylic acids with polyhydric alcohols and vinyl compounds as crosslinking agents, and also halogen-containing modifications thereof of low flammability.
23. Thermosetting acrylic resins, derived from substituted acrylic esters, such as epoxy-acrylates, urethane-acrylates or polyester acrylates.
24. Alkyd resins, polyester resins or acrylate resins in admixture with melamine resins, urea resins, polyisocyanates or epoxide resins as crosslinking agents.
25. Crosslinked epoxide resins which are derived from polyepoxides, for example from bis-glycidyl ethers or from cycloaliphatic diepoxides.
26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methylcellulose.
27. Mixtures of polymers as memtioned above, for example PP/EPDM, Polyamide 6/EPDM or ABS, PVC/EVA, PVC/ABS, PVC/MBS, PC/ABS, PBTP/ABS.
28. Naturally occuring and synthetic organic materials which are pure monomeric compounds or mixtures of such compounds, for example mineral oils, animal and vegetable fats, oils and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.
29. Aqueous emulsions of natural or synthetic rubber, e.g. natural latex or latices of carboxylated styrene/butadiene copolymers.

In general, the stabilizers of this invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following.

1. ANTIOXIDANTS 1.1. Alkylated monophenols, for example 2,6-di-tert.butyl-4-methylphenol
2-tert.butyl-4,6-dimethylphenol
2,6-di-tert.butyl-4-ethylphenol
2,6-di-tert.butyl-4-n-butylphenol
2,6-di-tert.butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert.butyl-4-methoxymethylphenol 1.2. Alkylated hydroquinones, for example 2,6-di-tert.butyl-4-methoxyphenol
2,5-di-tert.butyl-hydroquinone
2,5-di-tert.amyl-hydroquinone
2,6-diphenyl-4-octadecyloxyphenol 1.3. Hydroxylated thiodiphenyl ethers, for example 2,2'-thio-bis-(6-tert.butyl-4-methylphenol)
2,2'-thio-bis-(4-octylphenol)
4,4'-thio-bis-(6-tert.butyl-3-methylphenol)
4,4'-thio-bis-(6-tert.butyl-2-methylphenol)

1.4. Alkyliden-bisphenols, for example 2,2'-methylene-bis-(6-tert.butyl-4-methylphenol)
2,2'-methylene-bis-(6-tert.butyl-4-ethylphenol)
2,2'-methylene-bis-[4-methyl-6-(-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6-tert.butyl-2-methylphenol)
1,1-bis-(5-tert.butyl-4-hydroxy-2-methylphenyl)-butane
2,6-di-(3-tert.butyl-5-methyl-2-hydroxybenzyl)-4-methylphenol
1,1,3-tris-(5-tert.butyl-4-hydroxy-2-methylphenyl)-butane
1,1-bis-(5-tert.butyl-4-hydroxy-2-methylphenyl)-3-n-dodecylmercaptobutane
ethylenglycol-bis-[3,3-bis-(3'-tert.butyl-4'-hydroxyphenyl)-butyrate]
di-(3-tert.butyl-4-hydroxy-5-methylphenyl)-dicyclopentadiene
di-[2-(3'-tert.butyl-2'-hydroxy-5'-methyl-benzyl)-6-tert.butyl-4-methylphenyl]-terephthalate.

1.5. Benzyl compounds, for example 1,3,5-tri-(3,5-di-tert.butyl-4-hydroxybenzyl)-2,4,6-trimethylbenzene-di-(3,5-di-tert.butyl-4-hydroxybenzyl)sulfide
3,5-di-tert.butyl-4-hydroxybenzyl-mercapto-acetic acid isooctyl ester
bis-(4-tert.butyl-3-hydroxy-2,6-dimethylbenzyl)dithiolterephthalate
1,3,5-tris-(3,5-di-tert.butyl-4-hydroxybenzyl)-isocyanurate
1,3,5-tris-(4-tert.butyl-3-hydroxy-2,6-dimethylbenzyl)isocyanurate
3,5-di-tert.butyl-4-hydroxybenzyl-phosphoric acid-dioctadecyl ester
3,5-di-tert.butyl-4-hydroxybenzyl-phosphoric acid-monoethyl ester, calcium-salt

1.6. Acylaminophenols, for example 4-hydroxy-lauric acid anilide
4-hydroxy-stearic acid anilide
2,4-bis-octylmercapto-6-(3,5-tert.butyl-4-hydroxyanilino)-s-triazine
octyl-N-(3,5-di-tert.butyl-4-hydroxyphenyl)-carbaminate

1.7. Esters of
β-(3,5-di-tert.butyl-4-hydroxyphenyl)propionic acid with monohydric or polyhydric alcohols, for example

| | |
|---|---|
| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

1.8. Ester of
β-(5-tert.butyl-4-hydroxy-3-methylphenyl)propionic acid with monohydric or polyhydric alcohols, for example

| | |
|---|---|
| methanol | diethyleneglycol |
| octadecanol | triethyleneglycol |
| 1,6-hexanediol | pentaerytritol |
| neopentylglycol | tris-hydroxyethyl isocyanurate |
| thiodiethyleneglycol | di-hydroxyethyl oxalic acid diamide |

1.9. Amides of
β-(3,5-di-tert.butyl-4-hydroxyphenyl)propionic acid for example N,N'-di-(3,5-di-tert.butyl-4-hydroxyphenylpropionyl)-hexamethylendiamine
N,N'-di-(3,5-di-tert.butyl-4-hydroxyphenylpropionyl)-trimethylendiamine
N,N'-di-(3,5-di-tert.butyl-4-hydroxyphenylpropionyl)-hydrazine

2. UV absorbers and light stabilizers

2.1. 2-(2'-Hydroxyphenyl)-benztriazoles, for example the 5'-methyl-, 3',5'-di-tert.butyl-, 5'-tert.butyl-, 5'-(1,1,3,3-tetramethylbutyl)-, 5-chloro-3,',5'-di-tert.butyl-, 5-chloro-3'-tert.butyl-5'-methyl-, 3'-sec.butyl-5'-tert.butyl-, 4'-octoxy, 3',5'-di-tert.amyl-, 3',5'-bis(α,α-dimethylbenzyl)-derivative.

2.2. 2-Hydroxy-benzophenones, for example the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivative.

2.3. Ester of optionally substituted benzoic acids for example phenyl salicylate, 4-tert.-butyl-phenylsalicylate, octylphenyl salicylate, dibenzoylresorcinol, bis-(4-tert.-butylbenzoyl)-resorcinol, benzoylresorcinol, 3,5-di-tert.butyl-4-hydroxybenzoic acid 2,4-di-tert.butylphenyl ester and 3,5-di-tert.-butyl-4-hydroxybenzoic acid hexadecyl ester.

2.4. Acrylates, for example

α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxycinnamic acid methyl ester, N-(β-carbomethoxy-β-cyanovinyl)-2-methyl-indoline.

2.5 Nickel compounds, for example nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel dibutyldithiocarbamate, nickel salts of 4-hydroxy-3,5-di-tert.butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazol, optionally with additional ligands.

2.6. Sterically hindered amines, for example bis-(2,2,6,6-tetramethylpiperidyl)-sebacate bis-(1,2,2,6,6-pentamethylpiperidyl)-sebacate n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylendiamine and
4-tert.octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethylpiperazinone).

2.7. Oxalic acid diamides, for example 4,4'-di-octyloxyoxanilide, 2,2'-di-octyloxy-5,5'-di-tert-.butyl-oxanilide, 2,2'-di-dodecyloxy-5,5'-di-tert.butyloxanilide, 2-ethoxy-2'-ethyl-oxanilide, N,N'-bis (3-dimethylaminopropyl)oxalamide, 2-ethoxy-5-tert.butyl-2'-ethyloxanilide and its mixture with 2-ethoxy-2'-ethyl-5,4'-di-tert.butyloxanilide and mixtures of ortho- and para-methoxy-as well as of o- and p-ethoxy-disubstituted oxanilides.

3. Metal deactivators, for example

N,N'-diphenyloxalic acid diamide, N-salicylal-N'-salicyloylhydrazine, N,N'-bis-salicyloylhydrazine, N,N'-bis-(3,5-di-tert.butyl-4-hydroxyphenylpropionyl)-hydrazine, 3-salicyloylamino-1,2,4-triazole, bis-benzyliden-oxalic acid dihydrazide.

4. Phosphites and phosphonites, for example triphenyl phosphite, diphenylalkyl phosphites, phenyldialkyl phosphites, tri-(nonylphenyl)phosphite, trilauryl phosphite, trioctadecyl phosphite, di-stearylpentaerythritol diphosphite, tris-(2,4-di-tert.butylphenyl)phosphite, di-isodecylpentaerythritol diphosphite, di-(2,4-di-tert.butylphenyl)pentaerythritol diphosphite, tristearyl-sorbite triphosphite, tetrakis-(2,4-di-tert.butylphenyl)-4,4'-diphenylylendiphosphonite.

5. Compounds which destroy peroxide, for example esters of $\beta$-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythritol-tetrakis($\beta$-dodecylmercapto)-propionate.

6. Polyamide stabilizers, for example copper salts in combination with iodides and/or phosphorus compounds and salts of divalent manganese.

7. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example 4-tert.butyl-benzoic acid, adipic acid, diphenylacetic acid.

9. Fillers and reinforcing agents for example, calcium carbonate, silicates, glass fibres, asbestos, talc, kaolin, mica, barium sulfate, metal oxides and hydroxydes, carbon black, graphite.

10. Other additives, for example plasticizers, lubricants, emulsifiers, pigments, optical brighteners, flameproofing agents, anti-static agents, blowing agents and thiosynergists such as dilaurylthiodipropionate or distearylthiodipropionate.

The following examples illustrate the embodiments of this invention. In these examples, all parts given are by weight unless otherwise specified.

EXAMPLE 1

4-Hydroxy-2,2,6,6-tetramethyl-1H-phosphorinane (a)

4,4-Ethylenedioxy-1-phenyl-2,2,6,6-tetramethylphosphorinane

A flask equipped with a Dean-Stark trap was charged with a mixture of 150 mls of ethylene glycol, 0.73 grams p-toluenesulfonic acid and 800 mls toluene and then purged with nitrogen for one hour. To this mixture, 10 grams of 1-phenyl-2,2,6,6-tetramethyl-4-phosphorinanone (0.04 mole) were added. The two phase system was heated to reflux and 26 mls of a water-ethylene glycol azeotrope were collected over a 20 hour period. The reaction mixture was washed with saturated sodium bicarbonate, water, dried over anhydrous potassium carbonate, the solvent removed in vacuo, and the residue distilled under reduced pressure to give 9.2 grams (78%) of a colorless liquid, bp 134°–140° C. (0.3 mm Hg).

Calcd for $C_{17}H_{25}O_2P$: P, 10.6. Found: P, 10.6.

(b)

4,4-Ethylenedioxy-2,2,6,6-tetramethyl-1H-phosphorinane

A flame dried flask, under nitrogen was charged with a mixture of 8.0 grams (0.027 mole) of the 4,4-ethylenedioxy-1-phenyl-2,2,6,6-tetramethyl-phosphorinane, 0.8 grams (0.115 mole) shiny lithium metal and 40 mls anhydrous tetrahydrofuran. The mixture was heated to reflux for five minutes and then stirred at room temperature, the mixture turning deep red after thirty minutes. The reaction was stirred for 48 hours, cooled to $-10°$ C., quenched with water until the red color dissipated, and extracted with diethyl ether. The combined ether extracts were dried over anhydrous potassium carbonate, solvent removed in vacuo, and distilled under reduced pressure to give 1.6 grams (27% of a colorless liquid, bp 65°–69° C. (0.05 mm Hg).

High resolution mass spectra: Calcd. for $C_{11}H_{21}O_2P$: 216.1278: Found: 216.1278.

(c) 2,2,6,6-Tetramethyl-1H-Phosphorinane-4-one

A flask, under nitrogen, was charged with a mixture of 43.2 grams (0.2 mole) of the 4,4-ethylenedioxy-2,2,6,6-tetramethyl-1H-phosphorinane, 250 mls 3M aqueous HCl and 250 mls tetrahydrofuran which was stirred at room temperature for 20 hours. To this mixture, 100 mls water were added and the reaction was extracted three times with diethyl ether. The combined ether extracts were washed with brine, dried over anhydrous sodium sulfate, the solvent removed in vacuo, and distilled under reduced pressure to give 14.4 grams (42%) colorless liquid, bp 53°–56° C. (0.9 mm Hg).

High resolution mass spectra. Calcd. for $C_9H_{17}OP$: 172.1013. Found: 172.1015

(d) 4-Hydroxy-2,2,6,6-tetramethyl-1H-Phosphorinane

A flame dried flask, under nitrogen, was charged with a suspension of 9.4 grams lithium tetrahydroaluminate in one liter of dry tetrahydrofuran. The suspension was then treated with a solution of 20 grams (0.12 mole) of the 2,2,6,6-tetramethyl-1H-phosphorinane-4-one in 140 mls tetrahydrofuran at room temperature. The reaction was heated to 50° C. for three hours, cooled to $-15°$ C., and treated dropwise with 176 ml water. The resultant white suspension was treated with 100 grams magnesium sulfate to scavange excess water, filtered washing well with diethyl ether, the solvent removed in vacuo and the residue distilled under reduced pressure (bp 60°–64° C. at 0.3 mm Hg) to give 8.16 grams (37%) of a white solid, mp 47°–50° C.

EXAMPLE 2

Bis(2,2,6,6-tetramethyl-phosphorinan-4-yl)sebacate

A mixture of 2.75 grams (0.015 mol) of 4-hydroxy-2,2,6,6-tetramethyl-1H-phosphorinane, 1.65 grams (0.0072 mol) of dimethyl sebacate and 6 mg of lithium hydride was charged into a flask equipped with a Dean-Stark trap and Dewar condenser and was heated under a nitrogen atmosphere to 70° C. The pressure was gradually reduced to 11 mm Hg during which time the temperature was increased to 170° C. The reaction mixture was purified chromatographically to give 1.7 grams (47%) of a white solid, mp 58°–63° C.

Anal. Calcd. for $C_{28}H_{52}O_4P_2$: C, 65.3, H, 10.2. Found: C, 65.6; H, 9.9.

EXAMPLE 3

Bis(1-oxo-2,2,6,6-tetramethyl-phosphorinan-4-yl)sebacate

A stirred mixture of 4.0 grams (0.0078 mol) of the bis(2,2,6,6-tetramethyl-phosphorinan-4-yl)-sebacate in 40 mls of toluene at room temperature was combined with a solution of 1.8 grams (0.0155 mol) of 30% aqueous hydrogen peroxide in 40 mls of distilled water. Upon completion of reaction, as found by disappearance of the starting phosphine by thin layer chromatography, the reaction mixture was transferred to a separatory funnel and the two layers separated. The aqueous layer was extracted sequentially with three 40 ml portions of chloroform. The combined organic layers were washed with 40 ml of distilled water, dried over anhydrous sodium sulfate and concentrated in vacuo. The crude residue was purified chromatographically to give 1.2 g (29%) of white semi-solid; mass spectra: m/e 546 (Calculated 546).

EXAMPLE 4

3,5-Di-tert-butyl-4-hydroxy-dihydrocinnamic acid (2,2,6,6-tetramethylphosphorinan-4-yl)ester A flask equipped with a Dean-Stark trap and a dry ice condenser was charged with 4.7 grams (0.027 mol) of 4-hydroxy-2,2,6,6-tetramethyl-1H-phosphorinane, 7.9 grams (0.27 mol) of methyl-3,5-di-tert-butyl-4-hydroxy-dihydrocinnamate and 20 mg (2.5 mol) of lithium hydride. The mixture was stirred under nitrogen and heated at 120°–135° C. and 50 mm Hg until 1.2 mls (100% of theory) of distillate were collected. The reaction mixture was chromatographically purified to give 3.9 g (33%) of white solid, mp 81°–84° C.

Calcd. for $C_{26}H_{42}O_3P$: C, 72.0; H, 9.8; P, 7.1. Found: C, 72.1; H, 9.6; P, 6.9.

EXAMPLE 5

4-Hydroxy-1-oxo-2,2,6,6-tetramethyl-1H-phosphorinane

The compound of this example was obtained from the residue of Example 3 by chromatography to give 0.8 g (15%) of white solid mp 185°–190° C.

EXAMPLE 6

4-[N-(n-Propyl)amino]-2,2,6,6-tetramethyl-1H-phosphorinane (a)
4-[N-(n-Propyl)amino]-1-phenyl-2,2,6,6-tetramethyl-phosphorinane A flask, under nitrogen, was charged with a mixture of 12.4 grams (0.05 mole) of 1-phenyl-2,2,6,6-tetra methyl-4-phosphorinanone, 17.7 grams (0.30 mole) of n-propylamine, 1.89 grams (0.03 mole) of sodium cyanotrihydroborate, 20 mls of 5N methanolic hydrochloric acid and 150 mls of methanol. The mixture was stirred at ambient temperature for three days and then treated with 20 mls of conc. hydrochloric acid. The reaction mixture was concentrated in vacuo and 30 mls of water and 25 mls of diethylether were added. The layers were separated and to the aqueous layer was added 8 grams of solid sodium hydroxide. The resultant basic mixture was extracted sequentially with five 25 ml portions of diethylether. The combined extracts were dried over anhydrous sodium sulfate, the solvent removed in vacuo and the residue distilled under reduced pressure to give 11.2 grams (77% yield) of colorless liquid, b.p. 140°–144° C. (0.1 mm Hg)

Calcd. for $C_{18}H_{30}NP$: C, 74.2; H, 10.4; N, 4.8 Found: C, 74.3; H, 10.4; N, 4.6

(b)
4-[N-(n-Propyl)amino]-2,2,6,6-tetramethyl-1H-phosphorinane

The compound of Example 6(a) was reduced using the procedure of Example 1(b). 1R: 2280 cm$^{-1}$ (P-H).

EXAMPLE 7

Unstabilized polypropylene powder (Hercules PROFAX 6501) was thoroughly blended with 0.2%, by weight, of additive. The blended materials were then milled on a two roll mill at 182° C. for 5 minutes, after which time the stabilied polypropylene was sheeted from the mill and allowed to cool. The milled polypropylene was then cut into pieces and compression molded on a hydraulic press at 220° C. (175 psi) into 5 mil (0.13 mm) films. The sample was exposed in a fluorescent sunlight/black light chamber. Failure was determined when the films showed first signs of decomposition such as brown edges or cracking.

| Additive | Hours to Failure |
| --- | --- |
| None | 200–300 |
| Compound of Example 2 | 540 |
| Compound of Example 3 | 450 |

EXAMPLE 8

| Processing Stability of Polypropylene Base Formulation | |
| --- | --- |
| Polypropylene* | 100 parts |
| Calcium Stearate | 0.10 parts |

*PROFAX 6501 from Hercules Chemical

Stabilizers were solvent blended into the polypropylene base formulation as solutions in methylene chloride and, after removal of the solvent by evaporation at reduced pressure, the resin was extruded at 288° C. using the following extruder conditions:

| | Temperature (°C.) |
| --- | --- |
| Cylinder #1 | 260 |
| Cylinder #2 | 274 |
| Cylinder #3 | 288 |
| Die #1 | 288 |
| Die #2 | 288 |
| Die #3 | 288 |
| RPM | 100 |

During extrusion, the internal extruder pressure was determined using a pressure transducer. After each of the first, third and fifth extrusions, resin pellets were compression molded into 125 mil (3.2 mm) thick plaques at 193° C. and specimen yellowness index (YI) determined according to ASTM D1925-63T.

| Extrusion Temperature 288° C. | | | | | | |
| --- | --- | --- | --- | --- | --- | --- |
| | Transducer Pressure After Extrusion (psi) | | | YI Color After Extrusion | | |
| | 1 | 3 | 5 | 1 | 3 | 5 |
| None | 575 | 560 | 510 | 3.5 | 3.7 | 3.3 |
| 0.1% Compound of Ex. 4 | 690 | 720 | 705 | 3.5 | 6.9 | 8.1 |
| 0.05% Compound of Ex. 4 + 0.1% of Antioxidant A* | 725 | 755 | 750 | 4.4 | 5.2 | 5.6 |

*Neopentyltetrayl tetrakis [3-(3,5-di-tert-butyl-4-hydroxyphenyl)propanoate].

The indicated data illustrate the effective stabilizing performance of the instant compounds.

Summarizing, it is seen that this invention provides a novel class of stabilizer compounds. Variations may be made in proportions, procedures and materials without departing from the scope of the invention as defined by the following claims.

What is claimed is:

1. The compound of formula II

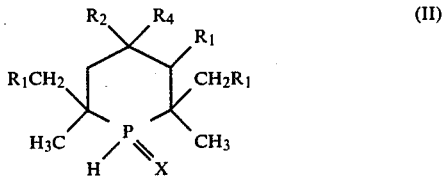

wherein $R_1$ and $R_2$ independently are hydrogen or $C_1$-$C_8$ alkyl, X is —O—, —S— or a lone pair of electrons, $R_4$ is hydroxy or a group —$NHR_3$, whereby $R_3$ is hydrogen or $C_1$-$C_{12}$ alkyl.

2. The compound of claim 1, wherein $R_1$ and $R_2$ are hydrogen.

3. The compound of claim 1, wherein X is —O— or a lone pair of electrons.

4. The compound of claim 1, wherein $R_4$ is hydroxy.

5. 4-Hydroxy-2,2,6,6-tetramethyl-1H-phosphorinane according to claim 1.

6. 4-Hydroxy-1-oxo-2,2,6,6-tetramethyl-1H-phosphorinane according to claim 1.

* * * * *